United States Patent [19]
Rausche et al.

[11] 4,347,743
[45] Sep. 7, 1982

[54] ACCELEROMETER MOUNTING ASSEMBLY

[75] Inventors: Frank Rausche, Aurora; Garland E. Likins, Jr., Newbury, both of Ohio

[73] Assignee: Pile Dynamics, Inc., Cleveland Heights, Ohio

[21] Appl. No.: 188,362

[22] Filed: Sep. 18, 1980

[51] Int. Cl.$^3$ ............................................. G01P 15/09
[52] U.S. Cl. .......................................... 73/654; 73/493
[58] Field of Search ................. 73/649, 654, 493, 644, 73/517 R; 310/328, 329

[56] References Cited
U.S. PATENT DOCUMENTS

| | | |
|---|---|---|
| 3,113,223 | 12/1963 | Smith et al. ........................ 310/329 |
| 3,309,915 | 3/1967 | McEuen et al. ...................... 73/654 |

FOREIGN PATENT DOCUMENTS 391407 11/1973 U.S.S.R. ............................... 73/649

*Primary Examiner*—James J. Gill
*Attorney, Agent, or Firm*—Pearne, Gordon, Sessions, McCoy & Granger

[57] ABSTRACT

An accelerometer assembly is disclosed which includes an accelerometer mounting block formed of a rigid material having a proportion of the modulus of elasticity to the density of less than 15,000,000 psi/lb/in$^3$. The natural frequency of the mounting block is safely below the accelerometer's response frequency but higher than the frequency to be recorded so that the mounting block does not resonate with high frequency vibrations and cause quick saturation of the accelerometer amplifier or erratic signals. The preferred mounting block is formed of polycarbonate, which is non-metallic, rigid, and lightweight, and has a natural frequency sufficiently below that of the accelerometer.

10 Claims, 3 Drawing Figures

ACCELEROMETER MOUNTING ASSEMBLY

BACKGROUND OF THE INVENTION

1. Field of the Invention

This invention relates to accelerometers, and more particularly to a unique mounting assembly which avoids problems of frequency interference.

2. Description of the Prior Art

Accelerometers are used in various applications to measure shock, vibration, acceleration or deceleration. Among the most popular types of accelerometers are piezoelectric accelerometers which comprise a mass acting upon a piezoelectric material. Accelerations move the mass to provide an electric indication from the piezoelectric material. Piezoelectric accelerometers are popular because they are very rugged and easily used. Often, these accelerometers include built-in amplifiers which increase their convenience. The mass in the piezoelectric accelerometers is usually undampened, but the accelerometers typically have a high natural frequency of greater than 30,000 Hertz (30 kHz), and usually greater than 40 kHz. Because the mass in the piezoelectric accelerometers is undampened, any high frequency vibration to which the accelerometer is subjected may be greatly amplified by the accelerometer.

In many applications, the accelerometer is mounted to the specimen to be monitored by means of a mounting block or other attaching device. For example, in U.S. Pat. No. 3,391,571, issued to Johanson, an accelerometer is attached to pavement by means of a tool which is driven into the pavement and has an attaching mechanism for the accelerometer. For another example, in pile capacity testing apparatus such as that shown in U.S. Pat. No. 3,960,008, the accelerometer is attached to a hammer which is dropped onto a concrete pile to determine the static load bearing capacity of the pile.

For either axial vibration or axial shock measurements, it is often necessary to mount the accelerometer parallel to the specimen to be monitored. This parallel mounting may be accomplished by using a mounting assembly comprising a block which is bolted or cemented to the specimen and has means for attaching the accelerometer to the block. A typical mounting block may be in the form of a small rectangular prism of approximately one to two inches in length which is formed of a rigid, secure, lightweight material.

A piezoelectric accelerometer may be operated up to frequencies close to its resonant point, which is usually in the neighborhood of 40 kHz. However, in order to obtain this high frequency response, the accelerometer needs a strong, rigid support with essentially direct contact between the accelerometer base and the surface of the specimen to which it is mounted. The accelerometer mounting block must not provide any cushioning or resilient effect which would isolate the accelerometer from the specimen and significantly reduce the high frequency response of the transducer. The mounting block must also be relatively lightweight to avoid attachment problems and the possibility of mass effects of the mounting block on the measured acceleration or vibration. For these reasons, aluminum has been used and has previously been considered the ideal material for the fabrication of accelerometer mounting blocks.

There is a major disadvantage or problem with aluminum mounting blocks. The natural frequency of the block is in the neighborhood of that of the accelerometer, i.e., about 40 kHz. Thus, incidental high frequency vibrations are amplified or reinforced by the combination of the mounting block and the accelerometer, causing quick saturation of the accelerometer amplifier or erratic signals which may make the lower level vibration or shock measurements difficult or impossible to read.

SUMMARY OF THE INVENTION

The disadvantages and problems of prior art mounting assemblies for accelerometers are overcome by the mounting assembly of the present invention. In accordance with the present invention, it has been determined that a material having the proper proportion of the modulus of elasticity to the density will, when used in the form of a small mounting block for the attachment of the accelerometer to the specimen to be monitored, have a natural frequency safely below that of the accelerometer's response frequency, thus reducing the adverse effects of high frequency vibrations encountered during measurement, which would otherwise saturate the amplifier and make the vibration or shock measurements difficult to read. For a typical high natural frequency accelerometer, such as a piezoelectric accelerometer having a natural frequency of greater than 30 kHz, and typically greater than 40 kHz, the desired proportion of the modulus of elasticity to the density should be less than 15,000,000 psi per pounds per cubic inch (psi/lb/in$^3$). The preferred material for the mounting block of the present invention is a non-metallic material so that the transducer is electrically isolated from the specimen, thereby eliminating ground loop problems, and so that thermal conduction between the specimen and the accelerometer is minimized. The preferred non-metallic material for the mounting block is polycarbonate. In addition, in accordance with the preferred form of the mounting assembly of the present invention, the mounting block may be chosen of such a size that it also serves for lead wire attachment to the accelerometer.

These and other advantages are accomplished by the present invention of an accelerometer assembly for attachment to a specimen to be monitored for acceleration, which comprises a mounting block and an accelerometer mounted to the block. The mounting block is capable of attachment to the specimen, and is formed of a rigid material of which the proportion of the modulus of elasticity to the density of the material is less than 15,000,000 psi/lb/in$^3$. The accelerometer has a natural frequency of greater than 30 kHz.

Preferably, the material of the mounting block is nonmetallic and is polycarbonate.

DETAILED DESCRIPTION OF THE PREFERRED EMBODIMENT

Figure 1:
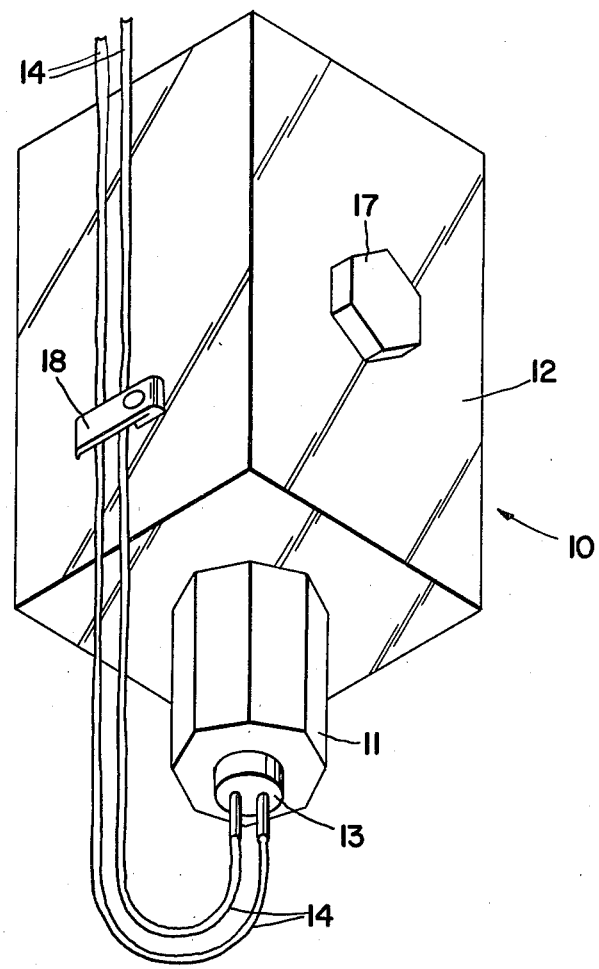
FIG. 1 is a perspective view of an accelerometer assembly which may be made in accordance with the present invention.

Referring more particularly to the drawings, FIG. 1 shows an accelerometer assembly 10 which comprises an accelerometer 11 attached to a mounting block 12. The accelerometer 11 is preferably a piezoelectric accelerometer of the type known in the art having a high natural frequency of greater than 30 kHz, and typically greater than 40 kHz. The accelerometer 11 may be equipped with a built-in amplifier. At one end of the accelerometer 11 is a solder cap 13 having terminals for attachment of lead wires 14 which may be soldered to the cap. The lead wires 14 extend from the accelerometer assembly to suitable apparatus which may be used to read the accelerometer output.

Figure 2:
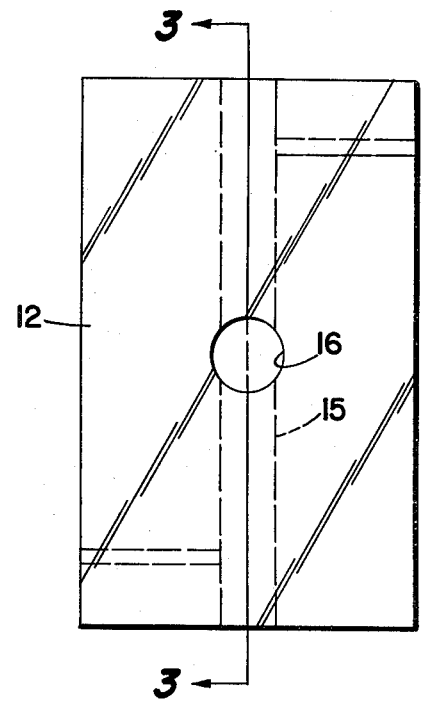
FIG. 2 is a side elevational view of the mounting block along line 2—2 of FIG. 1.
Figure 3:
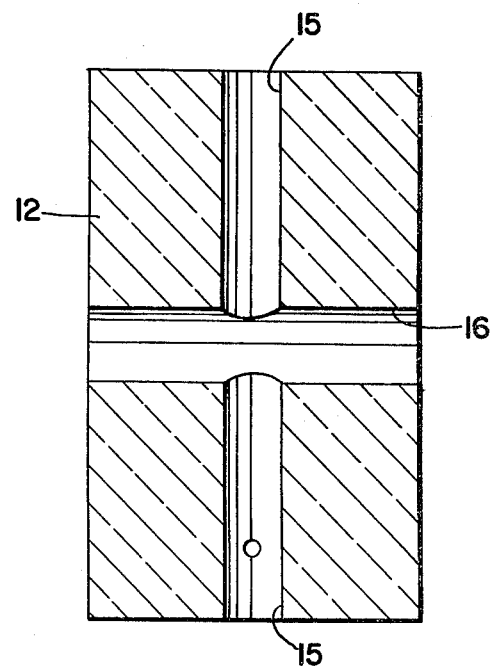
FIG. 3 is a cross sectioal view of the mounting block taken along line 3—3 of FIG. 2.

The accelerometer 11 is provided with a bolt or other means for attachment to the mounting block 12. The block 12 has a longitudinal bore hole 15 (FIGS. 2 and 3) for the accelerometer attachment. The block 12 provides a means for attaching the accelerometer 11 parallel to the specimen to be monitored. If the accelerometer 11 were directly mounted to the specimen without a mounting block, the accelerometer would be mounted perpendicular to the specimen. The mounting block 12 has a lateral opening 16 which may be used for attaching the block to the specimen, such as by insertion of a bolt 17 through the opening 16 or by filling the opening 16 with the cement. The mounting block 12 is generally in the shape of a rectangular prism, and is typically about one to two inches in length, and about one-half to one inch wide on each side. Preferably, the mounting block 12 has one or two additional lateral holes 18 for mounting of a clamp 19 along one side of the block. The clamp 19 is used to hold the lead wires 14.

In order to avoid mass effects on the measured acceleration, the mounting block 12 must be formed of a lightweight material. The mounting block must also provide the accelerometer with a strong, rigid support, so that vibrations and shocks from the specimen are directly transmitted to the accelerometer without any cushioning or resilient effect, which would tend to isolate the accelerometer from the specimen and reduce the high frequency response of the instrument.

For these reasons, aluminum was previously used as the most common material in the formation of accelerometer mounting blocks. However, when aluminum is formed into a block having the same approximate dimensions of the block 12, the resulting block has a natural frequency in the neighborhood of the response frequency of the piezoelectric accelerometer 11. Thus, an aluminum mounting block of suitable size and dimension has a natural frequency of approximately 40 kHz, which produces a resonant effect upon the natural frequency of the accelerometer.

A disadvantage of piezoelectric accelerometers is that they are undampened. Any high frequency component transmitted to the accelerometer is greatly amplified. Thus, high frequency vibrations produced during testing will be reinforced by the natural frequency of the aluminum mounting block, resulting in possible amplifier saturation and erratic signals which could affect the validity of the accelerometer measurements.

One possible approach to remedy the frequency response problems of the mounting block would be to change the geometry of the mounting block. However, it is necessary that the mounting block be as small as possible in most applications, since the clearance for the accelerometer placement is usually relatively small. In addition, a mounting block of an unusual configuration may be unstable, difficult to produce, or too large, resulting in a block which is too heavy.

In accordance with the present invention, it has been found that vibrational frequency bears the following proportional relationship:

$$f = k\sqrt{\frac{E}{\rho}}$$

where f is the vibrational frequency, E is the modulus of elasticity, $\rho$ is density, and k is a constant for a block of fixed dimensions, boundary conditions and modes. Thus, if it is desired to reduce the natural frequency of the mounting block while retaining the geometry of the block, it would be desirable to reduce the modulus of elasticity or increase the density of the mounting block. However, as discussed previously, the mounting block should be lightweight to reduce mass effects on the measured acceleration, so that the density of the material should be reduced rather than increased.

In accordance with the present invention, it has been found that if the material for the mounting block is chosen so that the proportion of the modulus of elasticity to the density of the material is less than 15,000,000 psi/lb/in$^3$, the resulting natural frequency of the mounting block will be below the accelerometer's response frequency but higher than the frequency to be recorded, so that the natural frequency of the mounting block will not interfere with the vibration or shock measurements and a relevant signal can be obtained through electronic filtering. In addition, the material of the mounting block should be substantially rigid so that vibrations are transmitted directly from the specimen to the accelerometer, and the mounting block does not have any cushioning or resiliency effect which would tend to absorb vibrations and affect the validity of the accelerometer measurements. Preferably, the mounting block material should also be non-metallic to avoid problems of electrical and thermal conduction.

The preferred material for the mounting block 12 is polycarbonate. Polycarbonate resins are well known, and may be obtained, for example, under the trademark "Lexan" from General Electric Company. A comparison of the properties of polycarbonate and aluminum is shown in the following table:

| Material | Modulus of elasticity, E (psi) | Density, $\rho$ (lb/in$^3$) | E/$\rho$ (psi/lb/in$^3$) |
|---|---|---|---|
| Aluminum | 10,000,000 | 0.098 | 102,000,000 |
| Polycarbonate | 340,000 | 0.043 | 7,900,000 |

Since the proportion of the modulus of elasticity to the density for polycarbonate is 7,900,000 psi/lb/in$^3$, it satisfies the requirement of the present invention that this proportion be less than 15,000,000 psi/lb/in$^3$. Other non-metallic materials may be used for the mounting block 12. The materials should be chosen so that the proportion of the modulus of elasticity to the density is less than 15,000,000 psi/lb/in$^3$ so that the natural frequency of the mounting block is safely below the accelerometer's response frequency but higher than the frequency to be recorded.

In order for mechanical shock and vibration to be translated from the specimen to the accelerometer, the mounting block should be substantially rigid, and the material of the mounting block should also have a relatively high modulus of elasticity, preferably at least 100,000 psi. From the table above, it can be seen that polycarbonate is a substantially rigid material with a modulus of elasticity well above this limit. Other rigid materials may also be used.

In order to achieve a lightweight mounting block which will avoid mass effects on accelerometer measurements and which will still be large enough to accommodate the accelerometer and to securely attach the accelerometer to the specimen, the material of the mounting block should also have a relatively low density, preferably less than 0.2 lb/in$^3$. As shown above, the density of polycarbonate is less than this level, so that polycarbonate provides a suitable lightweight material.

In order to electrically and thermally isolate the accelerometer from the specimen, the material of the mounting block should also be non-metallic. If an electrically conductive material is used for the mounting block, such as aluminum, the accelerometer transducer may be subject to an electrical ground loop which would have an adverse effect on the output. These electrical ground loops appear as 60-cycle interference signals which are superimposed on the electrical output signal of the transducer and can affect the validity of the measurement and can be difficult to eliminate. Non-metallic materials, such as polycarbonate, also thermally isolate the accelerometer from the specimen so that the thermal effects encountered by the specimen will not be readily transmitted to the accelerometer.

An additional material property which may be significant in the mounting block of the present invention is internal damping. The material should be chosen with a suitable internal damping to avoid resonance at higher modes. It has been found that polycarbonate has internal damping properties which avoid this resonance.

The present invention has been described with respect to a specific embodiment thereof, and it would be obvious to those skilled in the art to which this invention pertains that various modifications and changes of this preferred embodiment may be made without departing from the spirit and scope of the invention as defined by the following claims.

What is claimed is:

1. An accelerometer assembly for attachment to a specimen to be monitored for acceleration which comprises:

a mounting block capable of attachment to the specimen, the block formed of a rigid material, the proportion of the modulus of elasticity to the density of the material being less than 15,000,000 psi/lb/in$^3$; and an accelerometer mounted to the block, the accelerometer having a natural frequency of greater than 30,000 Hertz.

2. An accelerometer assembly as defined in claim 1, wherein the mounting block material is non-metallic.

3. An accelerometer assembly as defined in claim 2, wherein the mounting block material is polycarbonate.

4. An accelerometer assembly as defined in claim 1, wherein the accelerometer is a piezoelectric accelerometer.

5. An accelerometer assembly as defined in claim 1, wherein the mounting block material has a density of less than 0.2 pounds per cubic inch.

6. An accelerometer assembly as defined in claim 1, wherein the mounting block material has a modulus of elasticity of greater than 100,000 pounds per square inch.

7. An accelerometer assembly as defined in claim 1, wherein the mounting block is between 0.5 and 3 inches long.

8. An accelerometer assembly as defined in claim 7, wherein the mounting block is between 0.25 and 2 inches wide on each side.

9. An accelerometer assembly for attachment to a specimen to be monitored for acceleration which comprises:

a mounting block capable of attachment to the specimen, the block being between 0.5 and 3 inches long and between 0.25 and 2 inches wide on each side, the block formed of polycarbonate material, the proportion of the modulus of elasticity to the density of the material being less than 15,000,000 psi/lb/in$^3$, the density of the material being less than 0.2 pounds per cubic inch, the modulus of elasticity of the material being greater than 100,000 pounds per square inch; and a piezoelectric accelerometer mounted to the block, the accelerometer having a natural frequency of greater than 30,000 Hertz.

10. An accelerometer assembly as defined in claim 1 or 9, wherein the accelerometer has lead wires extending therefrom and the mounting block has clamp means for attaching the lead wires.

* * * * *